United States Patent
Mohebi

(10) Patent No.: US 11,116,543 B2
(45) Date of Patent: Sep. 14, 2021

(54) SURGICAL INSTRUMENTS FOR HAIR TRANSPLANT

(71) Applicant: Parsa Mohebi, Encino, CA (US)

(72) Inventor: Parsa Mohebi, Encino, CA (US)

( * ) Notice: Subject to any disclaimer, the term of this patent is extended or adjusted under 35 U.S.C. 154(b) by 157 days.

(21) Appl. No.: 16/456,881

(22) Filed: Jun. 28, 2019

(65) Prior Publication Data

US 2020/0405350 A1 Dec. 31, 2020

(51) Int. Cl.
*A61B 17/34* (2006.01)
*A61F 2/10* (2006.01)
*A61B 17/00* (2006.01)

(52) U.S. Cl.
CPC ............ *A61B 17/3468* (2013.01); *A61F 2/10* (2013.01); *A61B 2017/00367* (2013.01); *A61B 2017/00752* (2013.01); *A61B 2017/00969* (2013.01)

(58) Field of Classification Search
CPC ....... A61F 2/10; A61B 17/34; A61B 17/3468; A61B 2017/00367; A61B 2017/00969
See application file for complete search history.

(56) References Cited

U.S. PATENT DOCUMENTS

| 10,758,272 | B1* | 9/2020 | Pak | A61B 17/3468 |
| 2004/0092924 | A1* | 5/2004 | Vasa | A61B 17/3468 606/32 |
| 2005/0096687 | A1* | 5/2005 | Rassman | A61B 17/3468 606/187 |
| 2005/0187573 | A1* | 8/2005 | Rassman | A61B 17/3468 606/187 |
| 2007/0106306 | A1* | 5/2007 | Bodduluri | A61B 34/10 606/133 |
| 2016/0120574 | A1* | 5/2016 | Shiao | A61F 2/10 606/187 |

\* cited by examiner

*Primary Examiner* — George J Ulsh
(74) *Attorney, Agent, or Firm* — Venable LLP

(57) ABSTRACT

A surgical instrument and method for implantation of follicular units into the scalp of a patient, includes a non-incising cylindrical tip attached to a distal end of a handle body, wherein the non-incising cylindrical tip defines a lumen and a slot for cradling a follicular unit in preparation for implantation. The lumen and the slot are configured to load a follicular unit through the slot into the lumen and to accommodate the loaded follicular unit in the lumen.

15 Claims, 10 Drawing Sheets

SURGICAL INSTRUMENTS FOR HAIR TRANSPLANT

BACKGROUND

1. Technical Field

The field generally relates to non-incising hand-held devices for implanting a follicular unit and methods of use thereof.

2. Discussion of Related Art

Over the past few years, great strides have been made to expedite and enhance the follicular unit excision (FUE) process, which is a process by which individual follicular units are harvested for implantation at an incision site on the scalp. As the number of patients seeking FUE continues to grow, many hair transplant surgeons recognize the need for this technique while also embracing its current shortcomings and developing more advanced technologies.

Standard handling includes forceps to hold and insert strip follicular unit transplantation (FUT) grafts, which are far more robust than FUE grafts. However, handling fragile, skinny FUE grafts and placing them using forceps, could jeopardize the growth of the grafts by applying unnecessary stress upon them. Methods and devices are needed that would minimize a graft's time out of the body. A rapid continuous flow is achieved with simultaneous graft handling by multiple different team members, by which grafts might be excised, counted, sorted, and placed via a rapid continuous circular flow. Incision sites are made by the surgeon prior to graft excision. The serial excision and placement loop began with the surgeon creating recipient sites and then harvesting grafts, so the placing team could insert them into the premade sites using a new type of dull, non-incisional implanters shortly thereafter. This method potentially minimized the time the grafts remained out of body.

Initially, sharp implanters were widely used but since sharps could be used only by surgeons, they required a team of one or two technicians to manually load the grafts into the implanters before the surgeon could simultaneously incise the skin and implant the grafts. This resulted in the procedure becoming even more dependent upon the surgeon as use of the sharp tip required the surgeon to incise the skin and insert grafts personally. Despite potentially reducing the overall time of the procedure, this device increased the time the surgeon had to spend in the operating room.

Next came the development of dull implanters, which possess a distinct advantage over sharp implanters because they do not require the surgeon to insert the grafts. In most countries, graft placing into premade incision sites can be done by technicians. Instead, incision sites are carefully premade in advance by the surgeon allowing one or two technicians to load the grafts while other technicians implant them into the incision site. This method, however, still requires two groups of technicians, with one group serving as loaders and the other group serving as implanters, thus resulting in a crowded procedure room and inefficiencies in the loading and implanting steps.

Thus, there remains a need for a device and method that simultaneously reduces damage to the harvested follicular unit and allows for the rapid loading and implanting of the graft to be conducted by a single technician to reduce inefficiencies, while also allowing for multiple grafts to be implanted simultaneously by more than one technician or surgeon at a time.

SUMMARY

An embodiment of the instant disclosure herein relates to a hand-held device for implanting a follicular unit having a handle body; a non-incising cylindrical tip attached to a distal end of the handle body; and a finger-actuated plunger mechanically coupled to the non-incising cylindrical tip. In such an embodiment, the non-incising cylindrical tip defines a lumen and a slot, where the lumen and the slot are configured to load a follicular unit through the slot into the lumen and to accommodate the loaded follicular unit in the lumen. Also, the finger-actuated plunger is mechanically coupled to the non-incising cylindrical tip such that when the finger-actuated plunger is in an actuated configuration at least a portion of the finger-actuated plunger is inserted into the lumen of the non-incising cylindrical tip.

An embodiment of the instant disclosure herein relates to a method for hair transplantation in a subject including the steps of creating an incision site in a target tissue location of the subject; loading a harvested follicular unit into a hand-held device for implanting the follicular unit; and implanting the harvested follicular into the incision site. In such an embodiment, the hand-held device includes a handle body; a non-incising cylindrical tip attached to a distal end of the handle body, the non-incising cylindrical tip defining a lumen and a slot, where the lumen and the slot are configured to load the follicular unit through the slot into the lumen and to accommodate the loaded follicular unit in the lumen; and a finger-actuated plunger mechanically coupled to the non-incising cylindrical tip such that when the finger-actuated plunger is in an actuated configuration at least a portion of the finger-actuated plunger is inserted into the lumen of the non-incising cylindrical tip. Also, implantation of the harvested follicular unit includes inserting the non-incising cylindrical tip of the loaded hand-held device into the incision site and actuating the finger-actuated plunger such that the loaded follicular unit egresses the non-incising cylindrical tip and is implanted into the incision site.

BRIEF DESCRIPTION OF THE DRAWINGS

Further objectives and advantages will become apparent from a consideration of the description, drawings, and examples.

DETAILED DESCRIPTION

Figure 1:
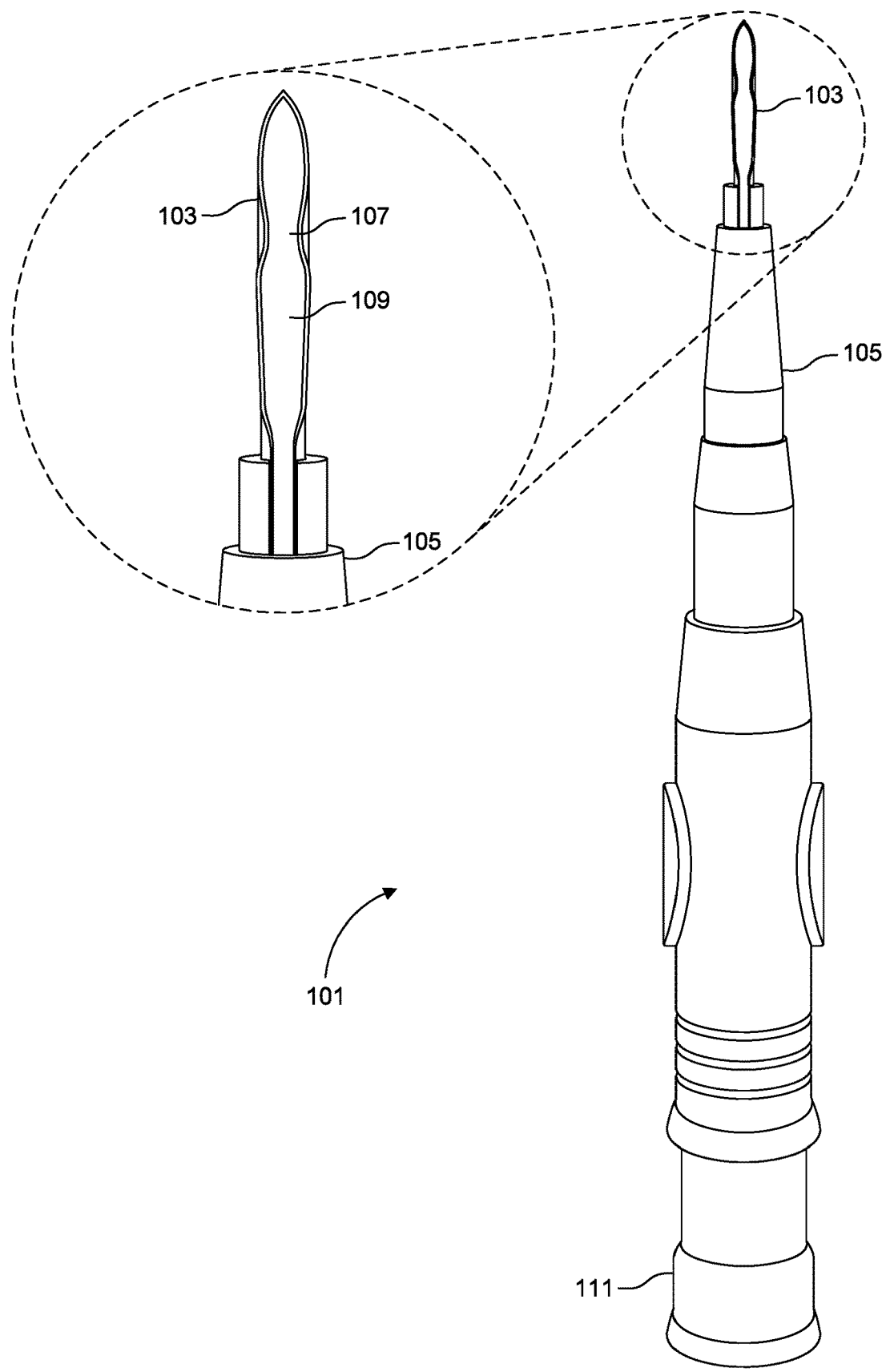
FIG. 1 is an illustration depicting a front view of a hand-held device for implanting a follicular unit, with a close-up of a non-incising cylindrical tip attached to the hand-held device's body according to an embodiment of the disclosure herein.

Some embodiments of the current disclosure herein are discussed in detail below. In describing embodiments, specific terminology is employed for the sake of clarity. However, the disclosure herein is not intended to be limited to the specific terminology so selected. A person skilled in the relevant art will recognize that other equivalent components can be employed and other methods developed without departing from the broad concepts of the current disclosure herein. All references cited anywhere in this specification, including the Background and Detailed Description sections, are incorporated by reference as if each had been individually incorporated.

The terms "graft" and "follicular unit" are used interchangeably throughout. In general, the terms "graft" and "follicular unit" refer to any piece of hair-bearing tissue that can be transplanted. A harvested graft or follicular unit is a piece of hair-bearing tissue that has been removed from one area and is to be implanted or otherwise transplanted into a separate area. Methods of harvesting grafts or follicular units are known in the art.

The terms "subject" and "patient" are used interchangeably throughout. In general, the terms "subject" and "patient" refer to an individual in need of or in want of a hair transplantation procedure.

The term "target tissue" as used throughout refers to a tissue location to be targeted for a hair transplantation procedure. In some cases, the target tissue is a region on the scalp of a patient or subject. However, the target tissue is not limited to the scalp of a patient or subject and can include other areas of the patient's or subject's epidermis and underlying dermis. The term "incision site" refers to a site on the target tissue which has been surgically manipulated to receive a graft.

The term "technician" as used throughout refers to an individual trained in a technical skill involved in a medical procedure (e.g. a hair-transplant procedure). In some instances, the technician is an individual other than a surgeon. In some instances, the technician is referred to as a "loader" and assists with and/or carries out the loading of a graft onto a medical device. In some instances, the technician is referred to an "implanter" and assists with and/or carries out the implanting of a graft into an incision site. In some cases, the technician can serve multiple roles including that of a "loader" and of an "implanter."

Hair transplantation surgery has dramatically improved over the past decade thanks to the emergence of new techniques of follicular unit transplantation (FUT) and follicular unit excision (FUE) allowing for greater efficiency and improved safety.

Sharp implanter devices have been developed because in some countries both the recipient incision site and also the graft implantation has to be performed by the surgeon personally. The popularity of FUE hair transplantation has provoked the development of more advanced devices that potentially increase the speed of the hair transplant procedure. It is now possible to perform larger FUE procedures in shorter timespans. Multiple options regarding punch devices have evolved in addition to progress in implanter technology.

The reduction in the size of the punch and the extraction part of the procedure both result in more fragile grafts versus those grafts obtained via strip harvesting. As a result, careful handling of the FUE grafts with forceps may be difficult or too slow. Many surgeons think that implanters may minimize injury to these delicate grafts while also increasing the speed of the procedure.

As an alternative to sharp implanter devices, various dull implanters have been developed. Dull implanters possess a distinct advantage over sharp implanters because they do not require the surgeon to insert the grafts. In most countries, graft placing into premade sites can be done by technical assistants. Instead, incisions are carefully premade in advance by the surgeon allowing one or two technicians to load the grafts while others inserted them. However, this step still lends itself to inefficiencies as two groups of technicians are still required with one group serving as the loaders and another group serving as the implanters.

More recent dull implanters have been developed, but these still present defects. For example, although some dull implanters allow for a single technician to load and implant the follicular unit, the technician must use both hands, thus limiting the operating area around a target tissue and preventing the simultaneous implanting of multiple follicle units by more than one technician. This limitation leads to inefficiencies ion the procedure including a slow-down in the procedure time.

Embodiments of the disclosure herein disclosed herein resolve the defects of the related art. More specifically, embodiments of the disclosure herein reduce inefficiencies in the loading and implanting of a follicular unit, and allow for increased space around a target tissue. This increase of space allows for the excising surgeon, the graft-extracting technician, and two implanting technicians to perform their tasks in limited space. Embodiments of the disclosure herein allow technicians to do at least the following: 1) load their own follicular units; 2) use only one hand for inserting the follicular units into pre-made incision sites; 3) comfortably switch hands depending of the angle of the incision site(s); and 4) keep their distance from the patient's head allowing for simultaneous graft excision and implanting into premade sites.

In general, embodiments of the disclosure herein are related to a dull implanter designed to reduce the manipulation of hair follicles during the implantation process into premade incision sites. Having premade incision sites allows two technicians to start implanting follicular units while the surgeon and a technician harvest the additional follicular units. One-handed placement of the follicular units with the device described herein allows the technicians to further distance themselves from the patient while decreasing the space to perform placement around the patient's head. This much needed space is crucial in maximizing the number of placers that can fit around the patient's head, and this is particularly true during the simultaneous excision and placement process.

Device

Embodiments of the hand-held device described throughout possess a narrow slot through which technicians may load their own follicular units before placing them just by rolling the device tip over the follicular units. Previous devices either had to be pre-loaded or required the use of two hands. Modifications, such as using loupes with a long focal point, allow for an adequate distance from the patient's head during placement. Maintaining an arm's-length working distance and the use of a single-hand implanter allow for simultaneous excision and placement into premade incision sites. With their one-person, one-hand design, embodiments of the hand-held device described throughout offer increased space around the patient and make implantation more efficient.

An embodiment of the instant disclosure herein relates to a hand-held device for implanting a follicular unit having a handle body; a non-incising cylindrical tip attached to a distal end of the handle body; and a finger-actuated plunger mechanically coupled to the non-incising cylindrical tip. In such an embodiment, the non-incising cylindrical tip defines a lumen and a slot, where the lumen and the slot are configured to load a follicular unit through the slot into the lumen and to accommodate the loaded follicular unit in the lumen. Also, the finger-actuated plunger is mechanically coupled to the non-incising cylindrical tip such that when the finger-actuated plunger is in an actuated configuration at least a portion of the finger-actuated plunger is inserted into the lumen of the non-incising cylindrical tip. As non-limiting examples, diameters of the non-incising tip may be produced in a range of sizes, such as external diameters of 0.6, 0.7, 0.8, 0.9 and 1 mm.

An embodiment of the instant disclosure herein relates to the hand-held device above, where the non-incising cylindrical tip further includes a blunt distal end.

An embodiment of the instant disclosure herein relates to the hand-held device above, where the slot is a tear-drop shaped slot.

An embodiment of the instant disclosure herein relates to the hand-held device above, where the slot extends the entire length of the non-incising cylindrical tip.

An embodiment of the instant disclosure herein relates to the hand-held device above, where the non-incising cylindrical tip has a length corresponding to at least a depth of a surgically-incised implantation site.

An embodiment of the instant disclosure herein relates to the hand-held device above, where the finger-actuated plunger when actuated has a sufficient length to insert into the lumen of the non-incising cylindrical tip so as to displace the loaded follicular unit and insert the loaded follicular unit into a surgically-incised implantation site.

An embodiment of the instant disclosure herein relates to the hand-held device above, where the lumen and the slot are configured to accommodate the follicular unit such that a bulb of the follicular unit is positioned towards a distal end of the non-incising cylindrical tip, and such that an end opposite the bulb of the follicular unit is positioned towards a proximal end of the non-incising cylindrical tip when the follicular unit is inserted into the non-incising cylindrical tip.

An embodiment of the instant disclosure herein relates to the hand-held device above, where the finger-actuated plunger comprises a first end extending from a posterior end of the handle body and a second end mechanically coupled to the non-incising cylindrical tip, and wherein when the finger-actuated plunger is configured such that actuation of the first end results in insertion of the second end into the lumen of the non-incising cylindrical tip.

FIG. 1 is an illustration depicting a front view of a hand-held device 101 for implanting a follicular unit (not shown), with a zoom-in of a non-incising cylindrical tip 103 attached to the hand-held device's body 105 according to an embodiment of the disclosure herein. The hand-held device of FIG. 1 includes a handle body 103; a non-incising cylindrical tip 103 attached to a distal end of the handle body 105, the non-incising cylindrical tip 103 defining a lumen 107 and a slot 109, where the lumen 107 and the slot 109 are configured to load a follicular unit (not shown) through the slot 109 and into the lumen 107 and to accommodate the loaded follicular unit (not shown) in the lumen 107. The hand-held device also includes a finger-actuated plunger 111 mechanically coupled to the non-incising cylindrical tip 103 such that when the finger-actuated plunger 111 is in an actuated configuration at least a portion of the finger-actuated plunger 111 is inserted into the lumen 107 of the non-incising cylindrical tip 103.

Figure 2:
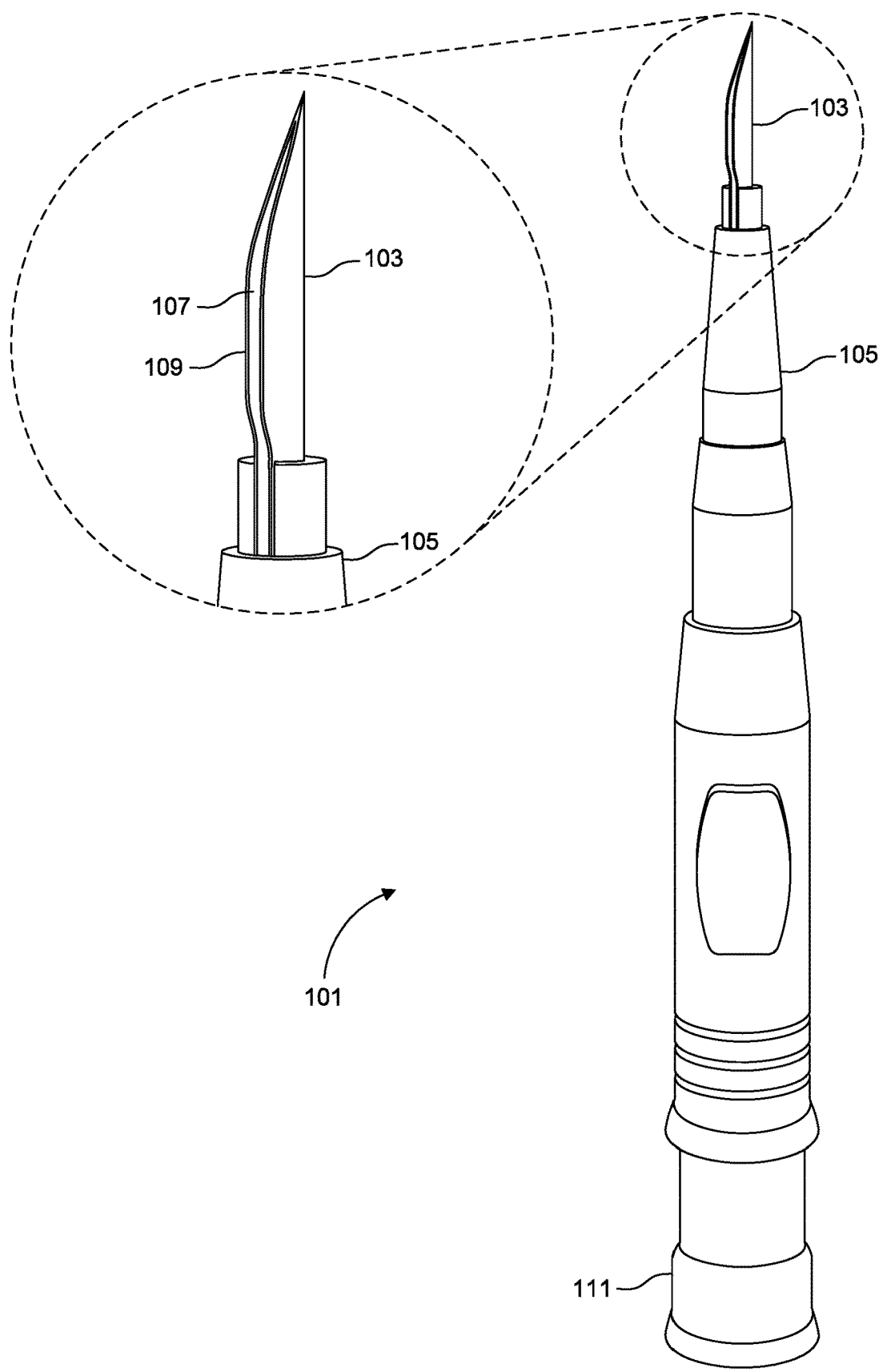
FIG. 2 is an illustration depicting a side view of a hand-held device for implanting a follicular unit, with a close-up of a non-incising cylindrical tip attached to the hand-held device's body according to an embodiment of the disclosure herein.
Figure 3:
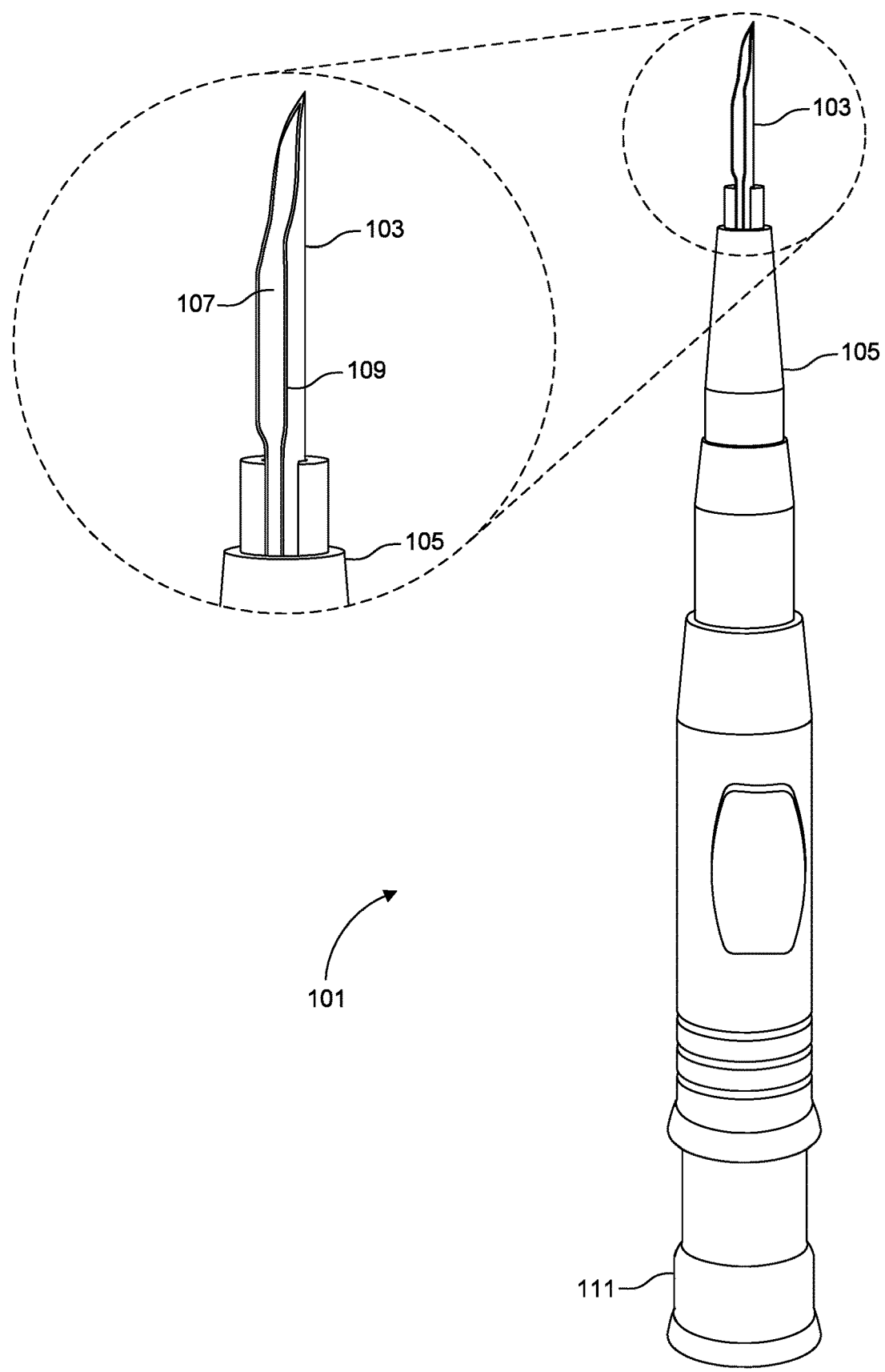
FIG. 3 is an illustration depicting a side view of a hand-held device for implanting a follicular unit, with a close-up of a non-incising cylindrical tip attached to the hand-held device's body according to an embodiment of the disclosure herein.

FIGS. 2 and 3 are illustrations depicting side views of the hand-held device 101 of FIG. 1, with a zoom-in of a non-incising cylindrical tip 103 attached to the hand-held device's body 105.

Figure 4A:
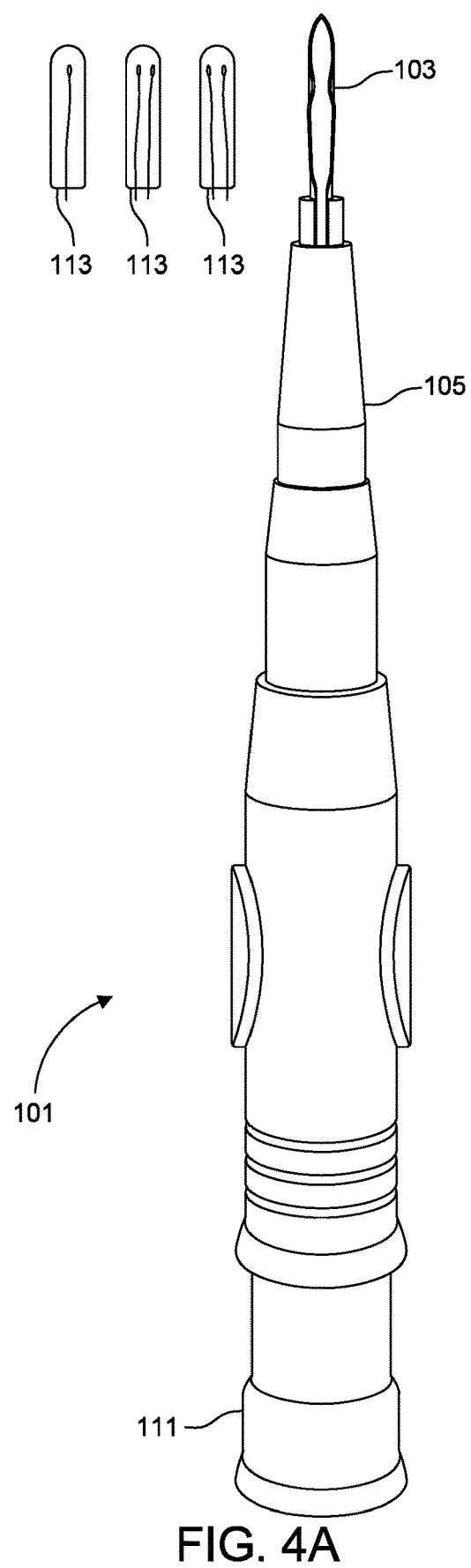
FIG. 4A is an illustration depicting a front view of a hand-held device for implanting a follicular unit according to an embodiment of the disclosure herein, with three follicular units, maintained alive and moist in a holding solution, located next to a non-incising cylindrical tip attached to the hand-held device's body.

FIG. 4A is an illustration depicting a front view of the hand-held device of FIG. 1, with three follicular units 113, maintained alive and moist in a holding solution, located next to a non-incising cylindrical tip 103 attached to the hand-held device's body 105.

Figure 4B:
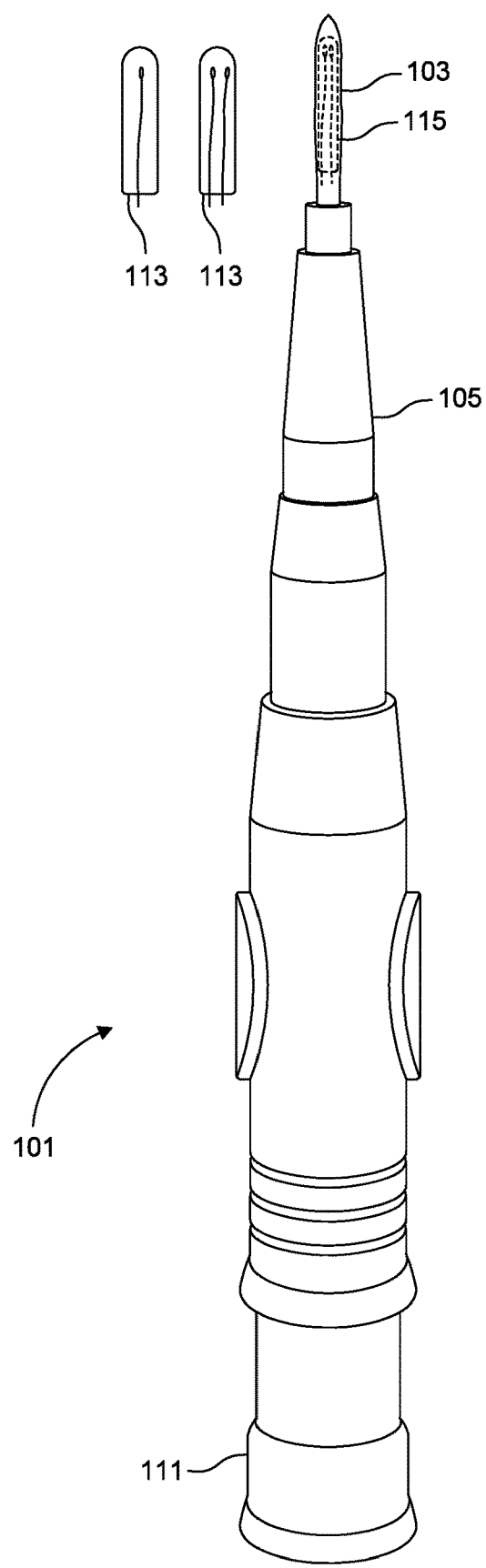
FIG. 4B is an illustration depicting a rear view of a hand-held device for implanting a follicular unit according to an embodiment of the disclosure herein, with a single follicular unit loaded into a non-incising cylindrical tip attached to the hand-held device's body.

FIG. 4B is an illustration depicting a rear view of the hand-held device of FIG. 1, with a single follicular unit 115 loaded into a non-incising cylindrical tip 103 attached to the hand-held device's body 105. Also, two follicular units 113 in solution are located next to the non-incising cylindrical tip 103.

Figure 4C:
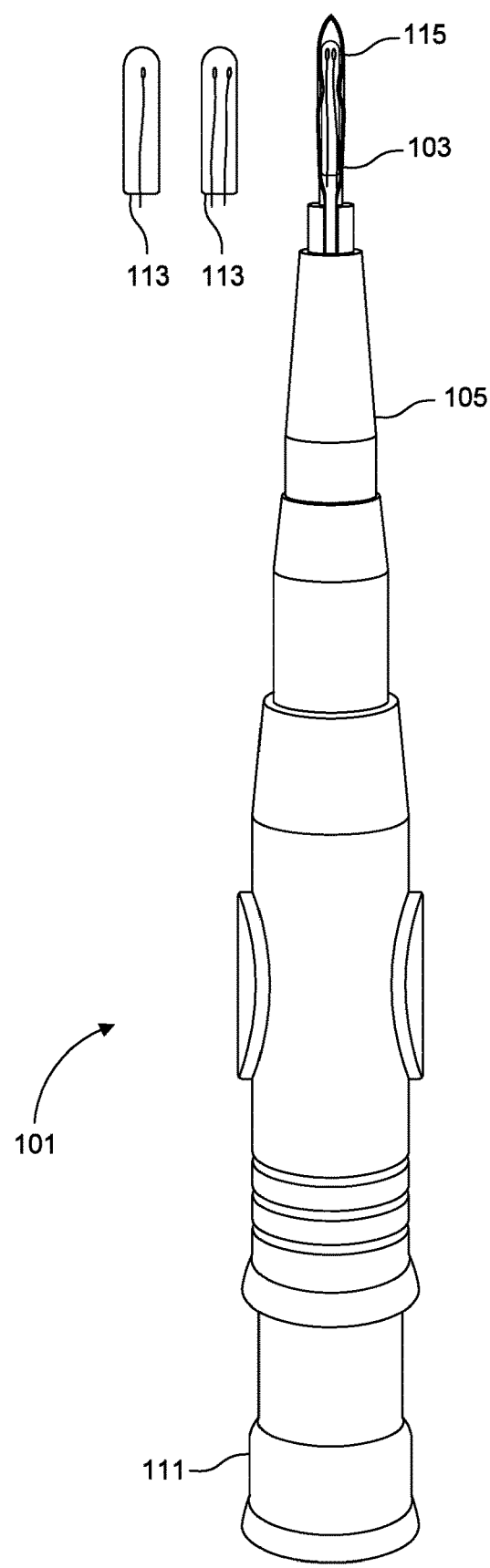
FIG. 4C is an illustration depicting a front view of a hand-held device for implanting a follicular unit according to an embodiment of the disclosure herein, with a single follicular unit loaded into a non-incising cylindrical tip attached to the hand-held device's body.

FIG. 4C is an illustration depicting a front view of the hand-held device of FIG. 4B, with a single follicular unit 115 loaded into a non-incising cylindrical tip 103 attached to the hand-held device's body 105. Also, two follicular units 113 in solution are located next to the non-incising cylindrical tip 103.

Method

An embodiment of the instant disclosure herein relates to a method for hair transplantation in a subject including the steps of creating an incision site in a target tissue location of the subject; loading a harvested follicular unit into a hand-held device for implanting the follicular unit; and implanting the harvested follicular into the incision site. In such an embodiment, the hand-held device includes a handle body; a non-incising cylindrical tip attached to a distal end of the handle body, the non-incising cylindrical tip defining a lumen and a slot, where the lumen and the slot are configured to load the follicular unit through the slot into the lumen and to accommodate the loaded follicular unit in the lumen; and a finger-actuated plunger mechanically coupled to the non-incising cylindrical tip such that when the finger-actuated plunger is in an actuated configuration at least a portion of the finger-actuated plunger is inserted into the lumen of the non-incising cylindrical tip. Also, implantation of the harvested follicular unit includes inserting the non-incising cylindrical tip of the loaded hand-held device into the incision site and actuating the finger-actuated plunger such that the loaded follicular unit egresses the non-incising cylindrical tip and is implanted into the incision site.

An embodiment of the disclosure herein relates to the method above, where both the loading step and the implanting step are carried out by a single individual.

An embodiment of the disclosure herein relates to the method above, where the loading of the harvested follicular unit into the hand-held device includes simultaneously loading a plurality of harvested follicular units into a plurality of hand-held devices, and where the simultaneous loading of the plurality of harvested follicular units into the plurality of hand-held devices is carried out at least in part by at least 2 individuals.

An embodiment of the disclosure herein relates to the method above, where the implanting of the harvested follicular unit further includes simultaneously inserting the plurality of loaded follicular units into a plurality of incision sites on the subject, and wherein the simultaneous insertion of the plurality of loaded follicular units is carried out at least in part by at least 2 individuals.

Some embodiments of the device described throughout have a unique loading system that can accommodate grafts of varying sizes. During graft loading, the technician holds the device in the dominant hand while grafts are arranged in a row over the other hand. A brief pre-sorting on the front end helps expedite loading the grafts into the non-incising cylindrical tip. The tip shaft has a unique teardrop-shaped slot on one side that is rotated downward to hover over the bulbs of the follicles. The non-incising cylindrical tip is then lowered so the bulbar ends of the grafts enter the opening. The next step is to gently push down and pull the non-incising cylindrical tip back, so that the grafts can smoothly enter the lumen of the non-incising cylindrical tip. A correctly loaded non-incising cylindrical tip has the bulbar end of the graft lying well protected within the lumen of the non-incising cylindrical tip while the graft's epidermal side can be out and visible.

After loading a graft, the dull tip of the non-incising cylindrical tip is gently inserted into the incision site previously made by the surgeon without actuating the finger-actuated plunger. The technician inserts the entire non-incising cylindrical tip into the incision site in order to identify the track of the premade incision site before actuating the finger-actuated plunger. Alternatively, only the distal 1 mm of the non-incising cylindrical tip is inserted before actuating the finger-actuated plunger.

When the non-incising cylindrical tip is positioned properly inside the incision, the plunger is actuated, directing the graft swiftly inside the incision site. The opening on top of the non-incising cylindrical tip is held upward during actuation of the plunger so the technician can visualize the location of the graft and be assured of the graft's proper implantation. Once the graft is in position, the technician rotates the non-incising cylindrical tip such that the skin cap lies parallel to the scalp. Depth control prevents the grafts from being buried. The graft skin cap must be oriented parallel to the skin and slightly above the surface. This allows the curvature of the grafts to follow a natural curve of the hair follicle in the area.

Depth control may be further effected from the collared extension of the body of the implanter over and around the neck of the tip. This collar limits the length of the tip that can enter the incision and allows the top portion of the skin from the graft to stay out of incision. Using depth control helps operators to be more efficient during implantation, as less care is needed to ensure a correct depth of implantation.

Figure 5:
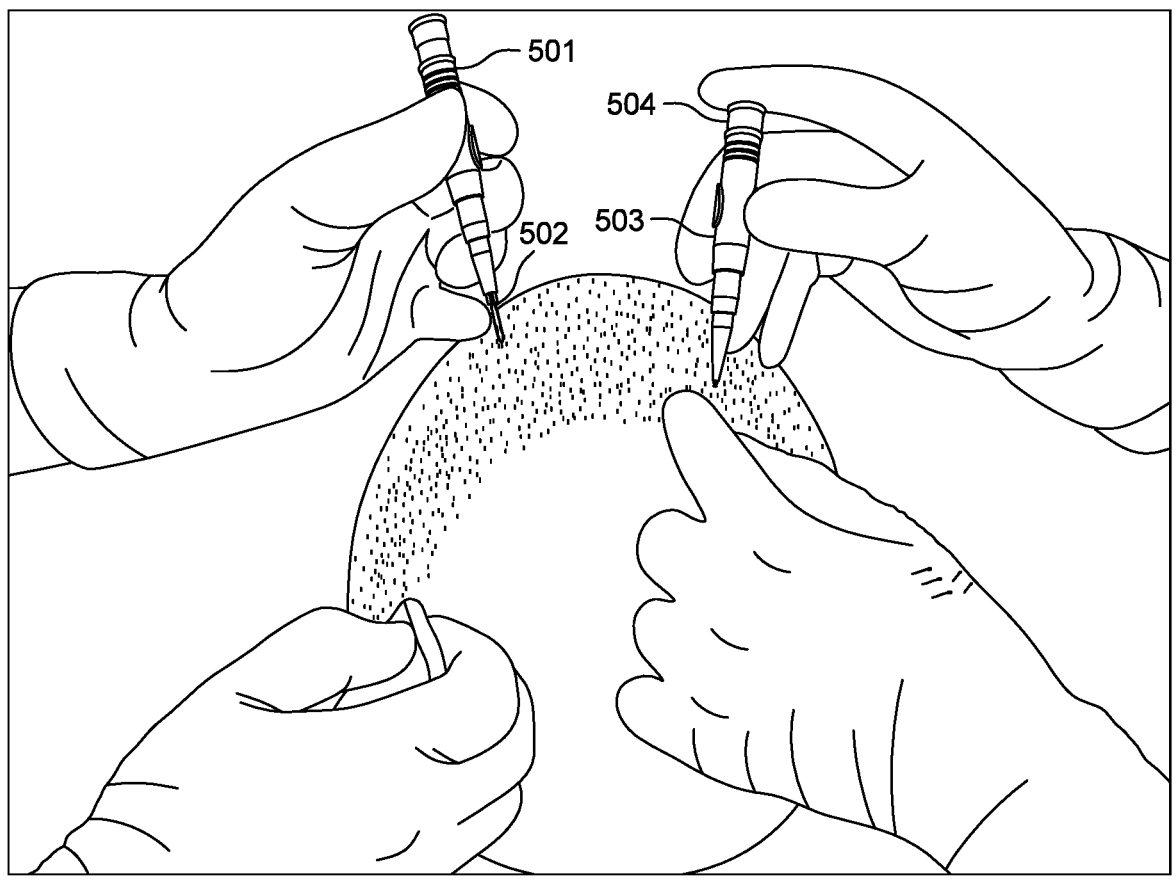
FIG. 5 is an illustration depicting the simultaneous implanting of two follicular units into a patient by two technicians via the use of two hand-held devices according to an embodiment of the disclosure herein.

FIG. 5 is an illustration depicting the simultaneous transplantation of two follicular units into the incisions in the patient's scalp by two technicians via the use of two hand-held devices 501, 503. More specifically, the technician using the device on the left 501 is inserting the non-incising tip 502 of the device that has been loaded with a follicular unit into a pre-made incision site. The technician using the device on the right 503 is inserting the non-incising tip of the device that has been loaded with a follicular unit into a pre-made incision site and has actuated the plunger 504 of the device so that the follicular unit is implanted into the pre-made incision site.

Figure 6:
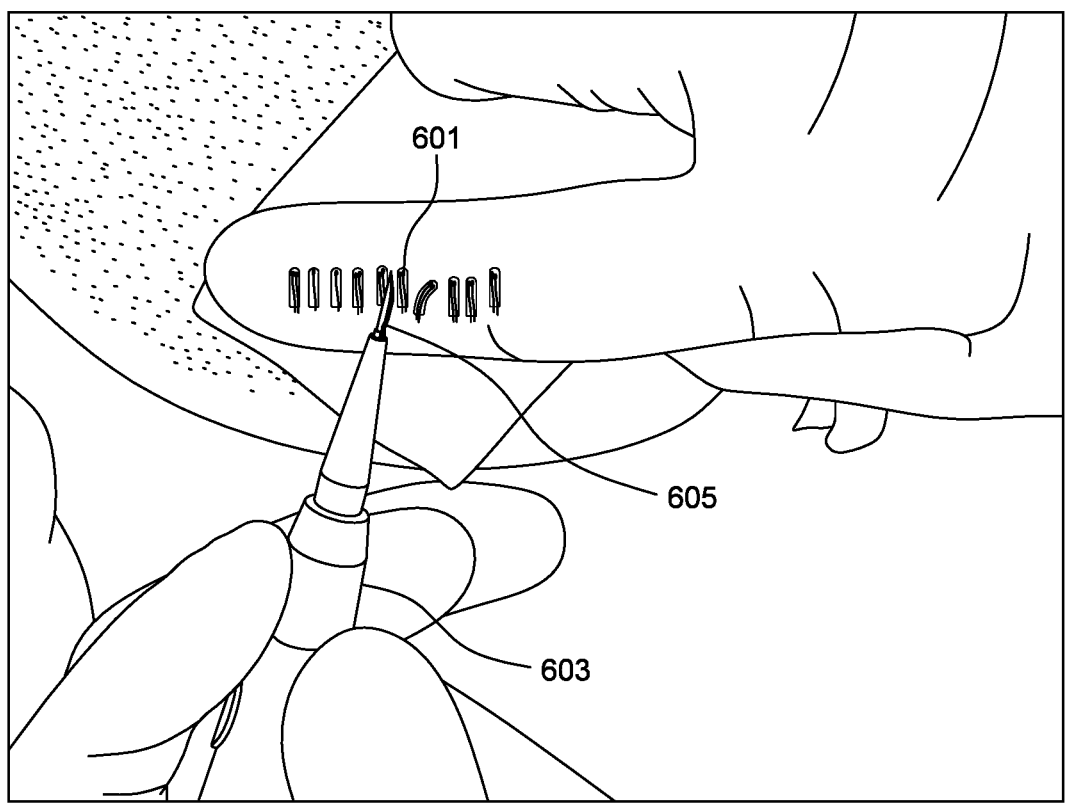
FIG. 6 is an illustration depicting the loading of a follicular unit into a hand-held device according to an embodiment of the disclosure herein.

FIG. 6 is an illustration depicting the loading of a follicular unit 601 into the non-incising cylindrical tip 603 of a hand-held device 605. In FIG. 6, a plurality of follicular units have been sorted. The non-incising cylindrical tip is then lowered onto a follicular unit so that the bulbar end of the follicular unit enters the opening of the tip.

Figure 7:
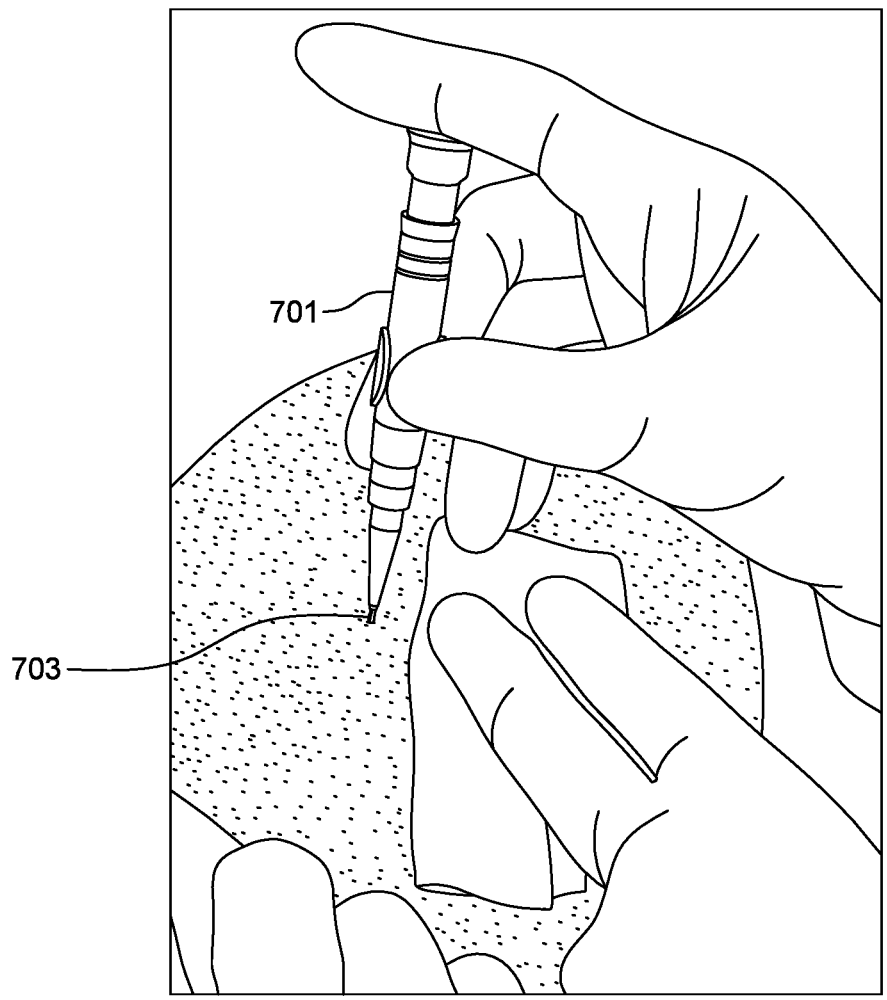
FIG. 7 is an illustration depicting the insertion of a loaded follicular unit into an incision site by a technician via the use of a hand-held device according to an embodiment of the disclosure herein.

FIG. 7 is an illustration depicting the insertion of a loaded follicular unit into an incision site by a technician. More specifically, the technician is using a hand-held device 701 and is inserting the non-incising tip 703 of the device that has been loaded with a follicular unit into a pre-made incision site.

Figure 8:
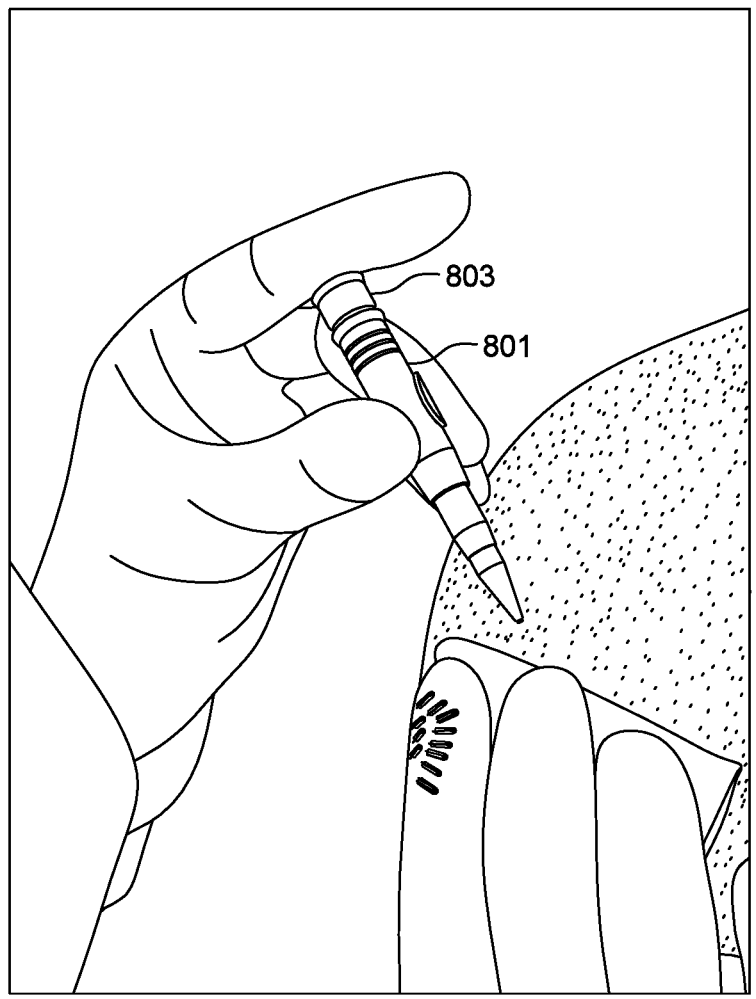
FIG. 8 is an illustration depicting implanting into an incision site a follicular unit loaded into a hand-held device by actuation of the hand-held device by a technician according to an embodiment of the disclosure herein.

FIG. 8 is an illustration depicting implanting into an incision site a follicular unit by a technician. More specifically, the technician is using a hand-held device 801 and has inserted a non-incising tip (not shown) of the device that has been loaded with a follicular unit into a pre-made incision site. The technician has actuated the plunger 803 of the device so that the follicular unit is implanted into the pre-made incision site.

The embodiments illustrated and discussed in this specification are intended only to teach those skilled in the art how to make and use the disclosure herein. In describing embodiments of the disclosure herein, specific terminology is employed for the sake of clarity. However, the disclosure herein is not intended to be limited to the specific terminology so selected. The above-described embodiments of the disclosure herein may be modified or varied, without departing from the disclosure herein, as appreciated by those skilled in the art in light of the above teachings. It is therefore to be understood that, within the scope of the claims and their equivalents, the disclosure herein may be practiced otherwise than as specifically described.

The invention claimed is:

1. A hand-held device for implanting a follicular unit comprising:
   a handle body;
   a non-incising cylindrical tip attached to a distal end of the handle body, the non-incising cylindrical tip defining a lumen and a slot, wherein the lumen and the slot are configured to load
   the follicular unit through the slot into the lumen and to accommodate the loaded follicular unit in the lumen; and
   a finger-actuated plunger mechanically coupled to the non-incising cylindrical tip such that when the finger-actuated plunger is in an actuated configuration at least a portion of the finger-actuated plunger is inserted into the lumen of the non-incising cylindrical tip, and wherein the handle body further comprises a collar adjacent the non-incising cylindrical tip, wherein the slot extends from a tip of the non-incising cylindrical tip to the collar;

wherein the slot of the non-incising cylindrical tip is positioned and dimensioned to facilitate single-handed loading of the follicular unit by rolling the device tip over the follicular unit.

2. The hand-held device of claim 1, wherein the non-incising cylindrical tip further comprises a blunt distal end.

3. The hand-held device of claim 1, wherein the slot is a tear-drop shaped slot.

4. The hand-held device of claim 1, wherein the non-incising cylindrical tip has a length corresponding to at least a depth of a surgically-incised implantation site.

5. The hand-held device of claim 1, wherein the finger-actuated plunger when actuated has a sufficient length to insert into the lumen of the non-incising cylindrical tip so as to displace the loaded follicular unit and insert the loaded follicular unit into a surgically-incised implantation site.

6. The hand-held device of claim 1, wherein the lumen and the slot are configured to accommodate the follicular unit such that a bulb of the follicular unit is positioned towards a distal end of the non-incising cylindrical tip, and such that an end opposite the bulb of the follicular unit is positioned towards a proximal end of the non-incising cylindrical tip when the follicular unit is inserted into the non-incising cylindrical tip.

7. The hand-held device of claim 1, wherein the finger-actuated plunger comprises a first end extending from a posterior end of the handle body and a second end mechanically coupled to the non-incising cylindrical tip, and wherein when the finger-actuated plunger is configured such that actuation of the first end results in insertion of the second end into the lumen of the non-incising cylindrical tip.

8. The hand-held device of claim 1, wherein the collar is positioned at a distance the non-incising cylindrical tip so as to effect depth control during implantation of the follicular unit into an incision by limiting the length of the non-incising cylindrical tip that can enter the incision to thereby allows a top portion of skin from the follicular unit to stay out of incision.

9. The hand-held device of claim 1, wherein the slot of the non-incising cylindrical tip remains open during implantation of the follicular unit.

10. The hand-held device of claim 1, wherein the slot of the non-incising cylindrical tip is positioned and dimensioned to facilitate single-handed loading of the follicular unit without use of forceps by rolling the device tip over the follicular unit.

11. The hand-held device of claim 1, wherein the slot of the non-incising cylindrical tip is positioned and dimensioned to facilitate single-handed loading of the follicular unit by rolling the device tip over the follicular unit, and wherein the finger-actuated plunger is configured to facilitate single-handed implantation of the loaded follicular unit into a surgically-incised implantation site.

12. A method for hair transplantation in a subject comprising:
creating an incision site in a target tissue location of the subject;
loading a harvested follicular unit into a hand-held device for implanting the follicular unit, the hand-held device comprising:
a handle body;
a non-incising cylindrical tip attached to a distal end of the handle body, the non-incising cylindrical tip defining a lumen and a slot, wherein the lumen and the slot are configured to load the follicular unit through the slot into the lumen and to accommodate the loaded follicular unit in the lumen; and
a finger-actuated plunger mechanically coupled to the non-incising cylindrical tip such that when the finger-actuated plunger is in an actuated configuration at least a portion of the finger-actuated plunger is inserted into the lumen of the non-incising cylindrical tip; and
implanting the harvested follicular unit by inserting the non-incising cylindrical tip of the loaded hand-held device into the incision site and actuating the finger-actuated plunger such that the loaded follicular unit egresses the non-incising cylindrical tip and is implanted into the incision site,
wherein the handle body further comprises a collar adjacent the non-incising cylindrical tip, wherein the slot extends from a tip of the non-incising cylindrical tip to the collar;
wherein the slot of the non-incising cylindrical tip is positioned and dimensioned to facilitate single-handed loading of the follicular unit by rolling the device tip over the follicular unit.

13. The method of claim 12, wherein both the loading step and the implanting step are carried out by a single individual.

14. The method of claim 12, wherein the loading a harvested follicular unit into a hand-held device comprises simultaneously loading a plurality of harvested follicular units into a plurality of hand-held devices, and wherein the simultaneous loading of the plurality of harvested follicular units into the plurality of hand-held devices is carried out at least in part by at least 2 individuals.

15. The method of claim 14, wherein the implanting the harvested follicular unit further comprises simultaneously inserting the plurality of loaded follicular units into a plurality of incision sites on the subject, and wherein the simultaneous insertion of the plurality of loaded follicular units is carried out at least in part by at least 2 individuals.

* * * * *